United States Patent [19]

Fusenig et al.

[11] 4,255,522
[45] Mar. 10, 1981

[54] PETRI DISH

[75] Inventors: Norbert Fusenig, Heidleberg; Wolfgang Thon, Essen, both of Fed. Rep. of Germany

[73] Assignee: Deutsches Krebsforschungszentrum, Heidelberg, Fed. Rep. of Germany

[21] Appl. No.: 51,239

[22] Filed: Jun. 22, 1979

[30] Foreign Application Priority Data

Jul. 1, 1978 [DE] Fed. Rep. of Germany ... 7819857[U]

[51] Int. Cl.³ .............................................. C12M 1/22
[52] U.S. Cl. .................... 435/297; 422/102; 435/301; 435/810
[58] Field of Search ............... 435/297, 298, 299, 300, 435/301, 801, 810; 422/102; 220/23.8

[56] References Cited

U.S. PATENT DOCUMENTS

| | | | |
|---|---|---|---|
| 3,097,070 | 7/1963 | Aldrich et al. | 435/297 X |
| 3,816,264 | 6/1974 | Winter et al. | 435/298 |
| 3,932,141 | 1/1976 | Beall et al. | 422/102 |
| 4,012,288 | 3/1977 | Lyman et al. | 435/301 X |
| 4,030,980 | 6/1977 | Beckford et al. | 435/300 X |
| 4,038,149 | 7/1977 | Liner et al. | 435/300 |
| 4,154,795 | 5/1979 | Thorne | 435/300 X |

*Primary Examiner*—Robert J. Warden
*Attorney, Agent, or Firm*—Spencer & Kaye

[57] ABSTRACT

A petri dish has on its bottom a plurality of zones surrounded by elevated ridges spatially separating the zones from one another.

3 Claims, 3 Drawing Figures

PETRI DISH

BACKGROUND OF THE INVENTION

This invention relates to a petri dish for receiving, growing and examining small amounts of cells or tissue. When working with primary cell cultures of epithelial origin or with small amounts of substance as initial material in a relatively large series of tests, the conventional way of growing cultures in petri dishes or flasks encounters difficulties because for such test series relatively large amounts of cells or substance are necessary which often cannot be accommodated.

SUMMARY OF THE INVENTION

It is an object of the invention to provide an improved petri dish which renders feasible the biochemical analysis of even limited amounts of primary cultures of epidermal cells.

This object and others to become apparent as the specification progresses, are accomplished by the invention, according to which, briefly stated, the bottom of the petri dish is divided into a plurality of zones which are spatially separated from one another by ridge-like elevations, such as ribs or rims.

A petri dish structured according to the invention results in a significant economy of the amount of cell or substance. With the aid of a single petri dish according to the invention, several values can be obtained, while a relatively small amount of cell material is used and while the manner of growth of the cells in the areas is directly comparable with that of cells grown in conventional petri dishes. The spatially separated cultures are grown in the same nutrient solution; this provides for additional possibilities of examining the mutual influence of growth of different cell types without direct contact. By cutting or punching the above-noted zones out of the dish bottom with the mini-cultures, the latter may be transferred into quantitatively corresponding receptacles for further processing for biochemical analyses. The dish bottom may be provided with weakened lines along the rims defining the individual zones, so that instead of cutting or punching, it is feasible to remove the bottom zones by breaking them out of the dish bottom.

DESCRIPTION OF THE PREFERRED EMBODIMENTS

Figure 1:
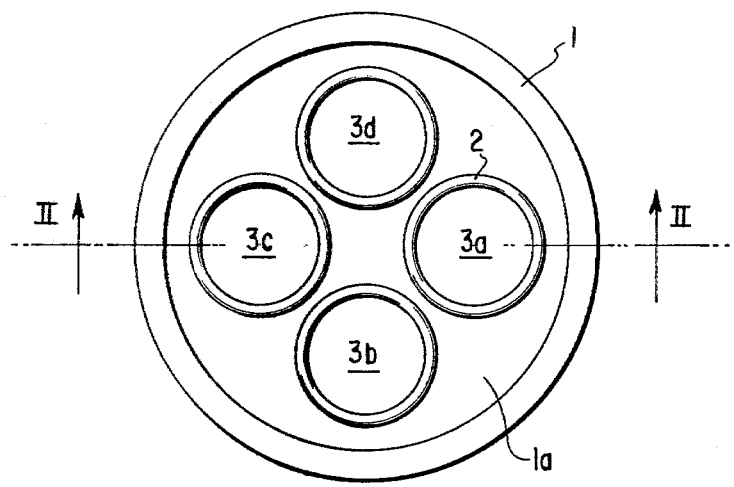
FIG. 1 is a top plan view of a preferred embodiment of the invention.
Figure 2:
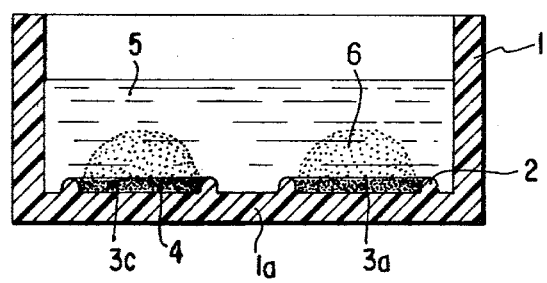
FIG. 2 is a sectional view taken along line II—II of FIG. 1.

Turning now to the Figures, the petri dish according to the invention comprises a dish-shaped vessel 1 having a bottom 1a. In the bottom 1a zones 3a, 3b, 3c and 3d are provided, each being bounded by a circular elevated rim or ridge 2. The zones in the example described may have a diameter of approximately 10 mm, while the dish has a diameter of 35 mm. Each zone is adapted to receive approximately 100 μl of a medium of a cell suspension 4. After adhesion of the cells, the dish bottom is covered with 2 ml of a nutrient solution 5, so that the cells can grow as indicated at 6. The growth of the cells 4, 6 in the spatially separated zones is not measurably different from the growth of cells grown in conventional petri dishes. In this manner four measuring values may be obtained from only one dish, while the amount of the cell material could be significantly reduced.

Figure 3:
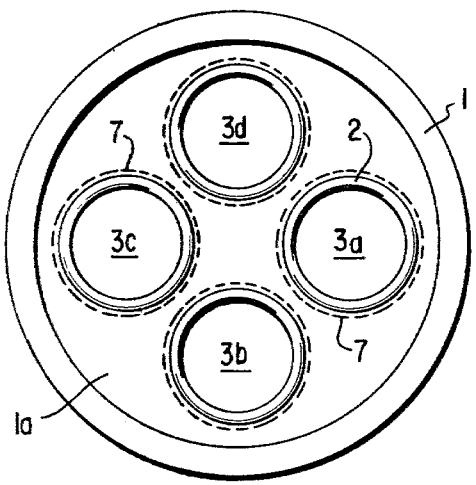
FIG. 3 is a top plan view of another preferred embodiment of the invention.

After growth, for further processing or additional analysis of the cultures, the bottom zones 3a–3d can be individually removed from the dish bottom. For this purpose, the dish bottom is of a plastic material such as, for example polystyrene which lends itself readily to a cutting or punching operation, or the dish bottom is provided with circular weakened lines along the rims 2, whereby the bottom zones can be readily broken out of the dish bottom. Such weakened lines, which are spaced from one another, are symbolically illustrated at 7 in FIG. 3.

It is to be understood that the above description of the invention is susceptible to various modifications, changes and adaptations, and the same are intended to be comprehended within the meaning and range of equivalents of the appended claims.

What is claimed is:

1. In a petri dish including a dish-shaped vessel having a bottom; the improvement comprising
    (a) a plurality of elevated ridges rising from said bottom; said ridges each having a closed configuration for defining separate, delimited bottom zones; and
    (b) weakened lines provided in said bottom; said weakened lines each having a closed configuration and each extending around a separate one of said ridges for permitting a removal of said bottom zones, together with the respective ridges, by breaking them out of said bottom.

2. A petri dish as defined in claim 1, wherein each said ridge and each said weakened line is circular.

3. A petri dish as defined in claim 1, wherein said weakened lines are spaced from one another.

* * * * *